(12) United States Patent
Yoshida

(10) Patent No.: US 9,039,604 B2
(45) Date of Patent: May 26, 2015

(54) ENDOSCOPE SYSTEM AND METHOD OF CONTROLLING ENDOSCOPE SYSTEM

(75) Inventor: Koji Yoshida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 4 days.

(21) Appl. No.: 13/565,645

(22) Filed: Aug. 2, 2012

(65) Prior Publication Data

US 2013/0053643 A1    Feb. 28, 2013

(30) Foreign Application Priority Data

Aug. 31, 2011  (JP) .................................. 2011-189672

(51) Int. Cl.

| | | |
|---|---|---|
| A61B 1/00 | (2006.01) | |
| A61B 1/12 | (2006.01) | |
| A61B 1/04 | (2006.01) | |
| A61M 37/00 | (2006.01) | |
| A61M 25/00 | (2006.01) | |
| A61M 5/32 | (2006.01) | |
| A61M 31/00 | (2006.01) | |
| A61B 17/34 | (2006.01) | |
| A61B 19/00 | (2006.01) | |

(52) U.S. Cl.
CPC ............. *A61B 1/00006* (2013.01); *A61B 1/126* (2013.01); *A61B 17/3421* (2013.01); *A61B 17/3474* (2013.01); *A61B 19/34* (2013.01)

(58) Field of Classification Search
USPC ................. 600/104–107, 114, 115, 117, 118, 600/121–125, 156–159; 604/23, 26, 264, 604/506–508, 510, 511, 513
See application file for complete search history.

(56) References Cited

U.S. PATENT DOCUMENTS

| | | | |
|---|---|---|---|
| 2007/0088275 A1* | 4/2007 | Stearns et al. ............ | 604/164.01 |
| 2008/0312638 A1 | 12/2008 | McNeil ......................... | 604/513 |
| 2009/0281478 A1 | 11/2009 | Duke ............................... | 604/22 |
| 2012/0101337 A1* | 4/2012 | Clark et al. ................... | 600/157 |

FOREIGN PATENT DOCUMENTS

| | | |
|---|---|---|
| JP | 5-86305 (U) | 11/1993 |
| JP | H 10-151202 (A) | 6/1998 |
| JP | 2008-538185 (A) | 10/2008 |
| JP | 2009-273883 (A) | 11/2009 |
| JP | 2011-120790 (A) | 6/2011 |
| WO | WO 2011/070845 (A1) | 6/2011 |

OTHER PUBLICATIONS

Notification of Reason(s) for Rejection dated Jul. 11, 2013, with English translation.

* cited by examiner

*Primary Examiner* — Ryan Henderson
(74) *Attorney, Agent, or Firm* — McGinn IP Law Group, PLLC

(57) ABSTRACT

An endoscope system including an endoscope insertion part to be inserted into a body cavity via a trocar stabbed in a body wall, the endoscope system comprising:
a detecting device detecting whether a tip of the endoscope insertion part has been drawn inside the trocar; and
a trocar cleaning device cleaning the inside of the trocar by supplying a predetermined fluid into the trocar when it is detected by the detecting device that the tip of the endoscope insertion part has been drawn inside the trocar.

8 Claims, 13 Drawing Sheets

ENDOSCOPE SYSTEM AND METHOD OF CONTROLLING ENDOSCOPE SYSTEM

BACKGROUND OF THE INVENTION

1. Field of the Invention

The present invention relates to an endoscope system and a method of controlling the endoscope system and, in particular, an endoscope system including an endoscope insertion part to be inserted into a body cavity via a trocar stubbed in a body wall and a method of controlling the endoscope system.

2. Description of the Related Art

Generally in a laparoscopic surgery, a trocar (an insertion instrument) is stubbed from the abdominal surface of an examinee into a body cavity, and then an insertion part of the laparoscope is inserted into the body cavity by using this trocar as a guide, thereby examining the presence or absence of an adhesion in the cavity or performing various treatments such as an adhesion treatment while observing a monitor display of a subject to be observed, such as an ovarian tumor or hysteromyoma. This laparoscopic surgery has advantages of being less invasive to a patient, compared with a laparotomy involving a large incision through an abdominal wall, and being able to create an expectation of early recovery.

An illumination window and an observation window are provided at the tip of an endoscope insertion part. With the inside of the body illuminated from the illumination window, the inside of the body cavity is observed via the observation window. Therefore, the observation window is required to be always in a clean state. However, smudges such as body fluids are attached to the surface of the observation window during an endoscopic examination. As a mechanism for cleaning the observation window of the endoscope insertion part, an injection nozzle may be provided. In this cleaning mechanism, a cleaning solution is injected from the injection nozzle to wash the smudges away from the surface of the observation window, and a compressed air is injected from the injection nozzle to blow drops of the remaining cleaning solution away from the surface of the observation window.

Meanwhile, in a laparoscopic surgery, there may be the case in which the smudges attached to the observation window cannot be sufficiently removed even when the observation window cleaning mechanism described above is used, resulting in a situation in which the field of surgical view is obstructed. In this case, for example, at the time of occurrence of view obstruction due to smudges of the observation window, the person performing surgery extracts the endoscope insertion part from the trocar and wipes the smudges off the observation window.

However, when the endoscope insertion part is extracted, the smudges such as blood and body fluids may be transferred into the trocar, and the smudges may be disadvantageously attached again to the observation window when the endoscope insertion part, having the smudges removed with an extra effort, is inserted into the body cavity via the trocar.

Japanese Patent Application Laid-Open No. 2009-273883 describes a technology of preventing a fluid in a trocar from depositing on a surgical instrument (for example, a laparoscope) inserted into the trocar. In this technology, a sensor for detecting the presence of a fluid or an instrument inside the trocar is provided. By vibrating the trocar according to an output from the sensor, the fluid in the trocar is prevented from depositing on the surgical instrument inserted into the trocar.

SUMMARY OF THE INVENTION

However, only vibrating the trocar as in the technology described in the patent gazette mentioned above cannot completely remove the smudges attached inside the trocar, although an effect of preventing attachment of the fluid in the trocar can be obtained to some degree. For this reason, the smudges attached inside the trocar may be attached again to the observation window of the endoscope insertion part inserted in the trocar.

Moreover, in the technology described in the patent gazette mentioned above, a mechanism for vibrating the trocar is required, thereby making the structure of the trocar complex and inviting an increase in diameter of the trocar and an increase in cost. These are not preferable for the trocar, which is desired to have a small diameter, as well as the endoscope insertion part.

The present invention was made in view of the circumstances described above, and has an object of providing an endoscope system and a method of controlling the endoscope system capable of keeping a good state of an observation window of an endoscope insertion part inserted into a body cavity via a trocar without requiring a special operation.

To achieve the object described above, an endoscope system according to the present invention includes an endoscope insertion part to be inserted into a body cavity via a trocar stabbed in a body wall, and the endoscope system includes detecting device detecting whether a tip of the endoscope insertion part has been drawn inside the trocar and trocar cleaning device cleaning the inside of the trocar by supplying a predetermined fluid into the trocar when it is detected by the detecting device that the tip of the endoscope insertion part has been drawn inside the trocar.

According to the present invention, when it is detected that the tip of the endoscope insertion part has been drawn inside the trocar, the fluid is injected into the trocar, thereby automatically cleaning the inside of the trocar. For this reason, when the endoscope insertion part is withdrawn from the trocar, the smudges attached to the observation window of the endoscope insertion part are not transferred to the trocar. Also, when the endoscope insertion part is inserted into the trocar after the smudges on the observation window of the endoscope insertion part are wiped off, the smudges attached inside the trocar is not attached again to the observation window of the endoscope insertion part. Therefore, the observation widow of the endoscope insertion part inserted into the body cavity via the trocar can be kept in a good state without performing a special operation.

In the present invention, the detecting device may be an optical, mechanical, or magnetic detection sensor or others.

In particular, in a preferable embodiment of the present invention, the detecting device preferably detects whether the tip of the endoscope insertion part has been drawn inside the trocar based on an endoscopic image obtained via an observation window disposed at the tip of the endoscope insertion part. According to this embodiment, whether the tip of the endoscope insertion part has been drawn inside the trocar is detected based on the endoscopic image, and therefore no special function is required to be added to the trocar. For this reason, it is possible to prevent an increase in diameter and cost of the trocar without making the structure of the trocar complex.

In a preferred embodiment of the present invention, the detecting device detects whether the tip of the endoscope insertion part has been drawn inside the trocar according to whether a tip opening of the trocar is included in the endoscopic image. According to this embodiment, it can be easily judged whether the tip of the endoscope insertion part has been drawn inside the trocar.

In a preferred embodiment of the present invention, an airtight preventive member is provided at base end side on inside of the trocar for ensuring airtightness of an insertion path into which the endoscope insertion part is inserted, and the detecting device detects whether the tip of the endoscope insertion part has been drawn inside the trocar according to whether the airtight preventive member is included in the endoscopic image. According to this embodiment, it can be easily judged whether the tip of the endoscope insertion part has been drawn inside the trocar.

In a preferred embodiment of the present invention, the trocar cleaning device intermittently supplies the fluid to the inside of the trocar when it is determined by the detecting device that the tip of the endoscope insertion part has been drawn inside the trocar. Also, the trocar cleaning device does not supply the fluid to the inside of the trocar when it is determined by the detecting device that the tip of the endoscope insertion part has not been drawn inside the trocar. According to this embodiment, the inside of the trocar can be reliably cleaned according to the operation of inserting or withdrawing the endoscope insertion part into or from the trocar.

In a preferred embodiment of the present invention, the trocar cleaning device may inject the fluid from an injection nozzle provided at the tip of the endoscope insertion part, or may inject the fluid from an injection nozzle provided at a tip of a sheath covering the endoscope insertion part. Also, the trocar cleaning device may supply the fluid to the inside of the trocar via a fluid introduction port provided at the trocar. In any embodiment, the inside of the trocar can be cleaned without adding a new function to the trocar.

In a preferred embodiment of the present invention, the trocar cleaning device cleans the inside of the trocar by selectively supplying a cleaning solution and a gas into the trocar. According to this embodiment, the inside of the trocar can be effectively cleaned.

Also, to achieve the object described above, a method of controlling an endoscope system including an endoscope insertion part to be inserted into a body cavity via a trocar stabbed in a body wall includes a detecting step of detecting whether a tip of the endoscope insertion part has been drawn inside the trocar and a trocar cleaning step of cleaning the inside of the trocar by supplying a predetermined fluid into the trocar when it is detected at the detecting step that the tip of the endoscope insertion part has been drawn inside the trocar.

In the present invention, in a preferred embodiment, whether the tip of the endoscope insertion part has been drawn inside the trocar is detected in the detecting step by using any of various sensors such as optical, mechanical, and magnetic sensors.

In particular, in the present invention, it is preferably detected in the detecting step whether the tip of the endoscope insertion part has been drawn inside the trocar based on an endoscopic image obtained via an observation window disposed at the tip of the endoscope insertion part.

According to the present invention, when it is detected that the tip of the endoscope insertion part has been drawn inside the trocar, the fluid is injected into the trocar, thereby automatically cleaning the inside of the trocar. For this reason, when the endoscope insertion part is withdrawn from the trocar, the smudges attached to the observation window of the endoscope insertion part are not transferred to the trocar. Also, when the endoscope insertion part is inserted into the trocar after the smudges on the observation window of the endoscope insertion part are wiped off, the smudges attached inside the trocar is not attached again to the observation window of the endoscope insertion part. Therefore, the observation widow of the endoscope insertion part inserted into the body cavity via the trocar can be kept in a good state without performing a special operation.

DETAILED DESCRIPTION OF THE PREFERRED EMBODIMENTS

Preferred embodiments of the present invention are described in detail below according to the attached drawings. While the case described herein is such that a laparoscope as a rigid endoscope is inserted into an abdominal cavity, with a trocar as a guide stabbed in an abdominal wall, for examination and treatment, the present invention can be applied also to various endoscopes other than the laparoscope. Furthermore, the applicable body part is not restricted to the inside of the abdominal cavity, and can be applied to any body part other the inside of the abdominal cavity as long as it is a closed space.

<First Embodiment>

Figure 1:
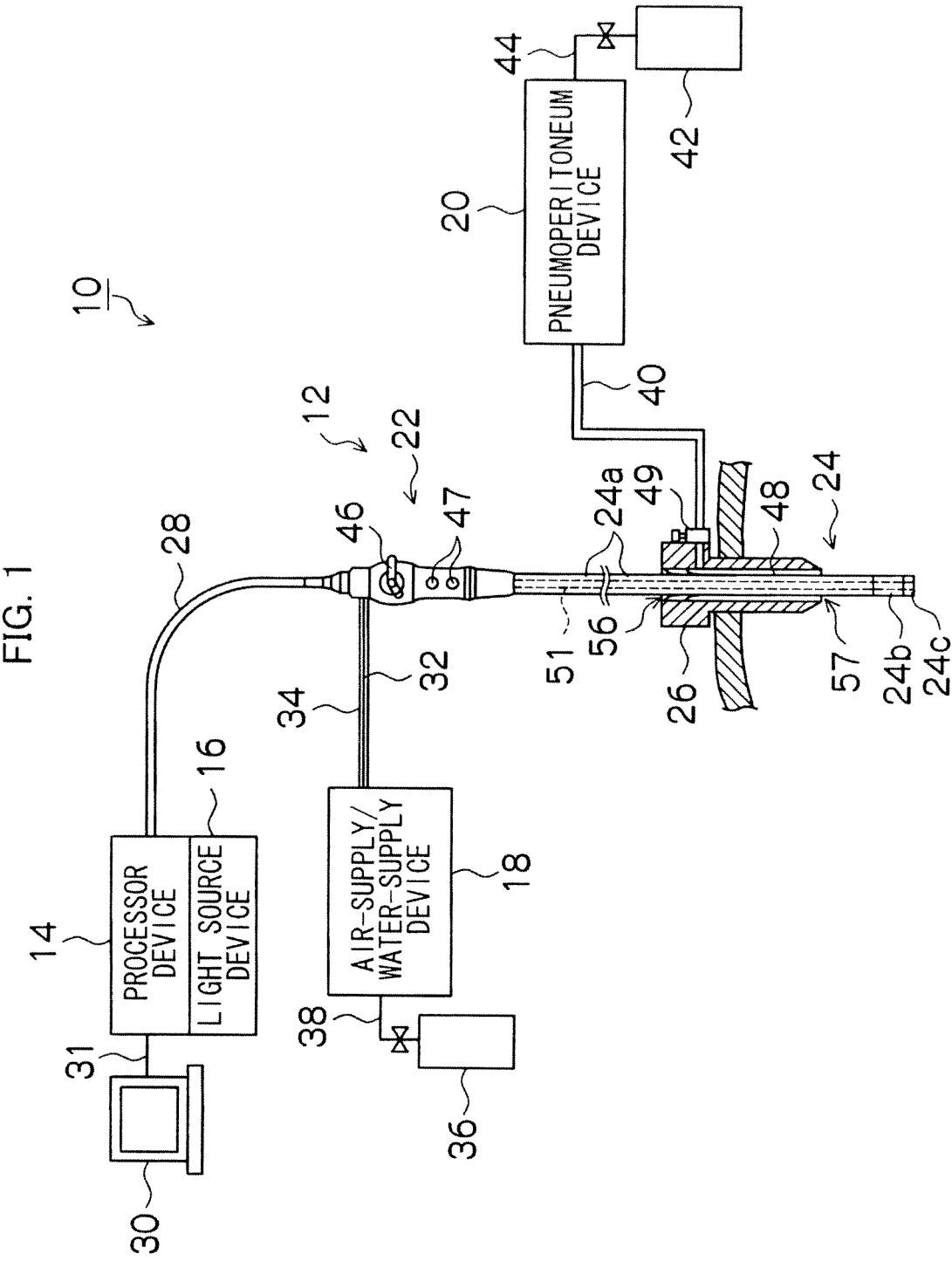
FIG. 1 is a schematic diagram of the structure of an endoscope system according to a first embodiment.

FIG. 1 is a schematic diagram of the structure of an endoscope system according to a first embodiment. As shown in FIG. 1, an endoscope system 10 of the present embodiment is mainly configured of a rigid endoscope 12, a processor device 14, a light source device 16, an air-supply/water-supply device 18, and a pneumoperitoneum device 20.

The rigid endoscope 12 includes a main body operating part 22 and an insertion part (hereinafter referred to as an "endoscope insertion part") 24 connected to this main body operating part 22. To the main body operating part 22, a universal cable 28 is connected. This universal cable 28 has a tip to which the processor device 14 and the light source device 16 are removably via a connector (not shown). The processor device 14 is also connected to a monitor 30 via a cable 31.

The main body operating part 22 is provided with an operating handle 46 and operation buttons 47 for performing various operations.

In the endoscope insertion part 24, a rigid part 24a, an angle part 24b and a tip rigid part 24c are connected in this order from the main body operating part 22. For examination and treatment inside the body cavity, most of the portion corresponding to the length of the endoscope insertion part 24 is occupied by the rigid part 24a. However, a soft endoscope can be used. In this case, the portion of the rigid part 24a is configured of a soft part. The angle part 24b is remotely operated to be curved by operating the operating handle 46 of the main body operating part 22. This allows the tip rigid part 24c to be oriented toward a desired direction.

Figure 2:
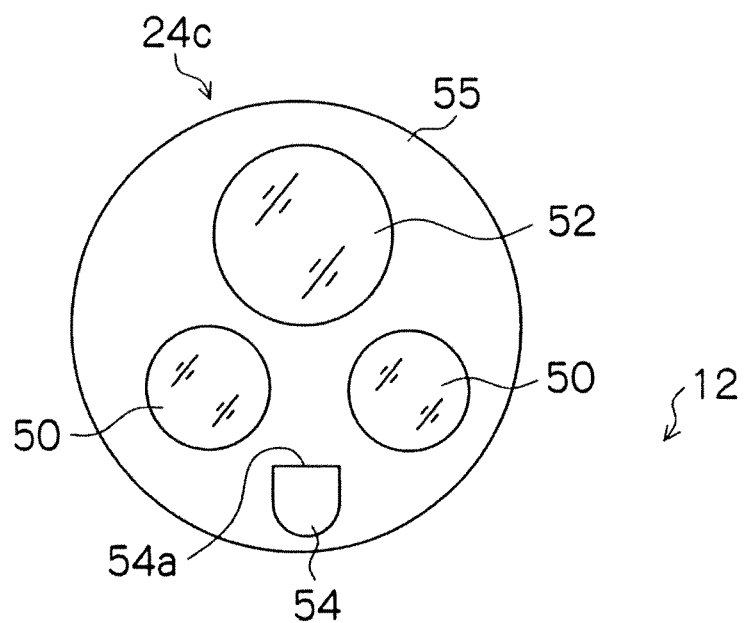
FIG. 2 is a plan view of a tip surface of an endoscope insertion part shown in FIG. 1.

As shown in FIG. 2, the tip rigid part 24c has a tip surface 55 provided with an observation window 52, illumination windows 50, and an injection nozzle 54. The observation window 52 configures a tip of an observation optical system. At the back of the observation window 52, a solid-state image pickup element (not shown) such as a CCD or a CMOS is disposed. This solid-state image pickup element is supported by a substrate to which a signal cable (not shown) is connected. The signal cable is inserted into the endoscope insertion part 24, the main body operating part 22, and the universal cable 28 shown in FIG. 1 and others to extend to a connector (not shown) to be connected to the processor device 14. With this, an observation image captured by the observation window 52 is formed on a light-receiving surface of the solid-state image pickup element to be converted to an electrical signal (an imaging signal), and this electrical signal is outputted via the signal cable to the processor device 14 to be converted to a video signal. Then, this video signal is outputted to the monitor 30 connected to the processor device 14, and an observation image (an endoscopic image) is displayed on a screen of the monitor 30.

An outgoing light end of a light guide (not shown) is disposed at the back of the illumination windows 50 of FIG. 2. This light guide is inserted into the endoscope insertion part 24, the main body operating part 22, and the universal cable 28, and has an incident light end disposed in the connector not shown. Therefore, with the connector connected to the light source device 16, illumination light emitted from the light source device 16 is transmitted via the light guide to the illumination windows 50, and is emitted ahead from the illumination windows 50. Note that while two illumination windows 50 are disposed on the tip surface 55 of the tip rigid part 24c in FIG. 2, the number of illumination windows 50 is not restrictive, and may be one or three or more.

The injection nozzle 54 is provided on the tip surface 55 of the tip rigid part 24c as means injecting a fluid such as a cleaning solution or a cleaning gas (a compressed air) for removing smudges such as blood and body fluids attached to the surface of the observation window 52. This injection nozzle 54 is configured to include an injection port 54a opening toward a direction approximately orthogonal to a longitudinal direction (an axial direction) of the endoscope insertion part 24 so that the observation window 52 is present in this opening direction of the injection port 54a. Inside the endoscope insertion part 24 and the main body operating part 22, a liquid-supply pipeline serving as a flow path for the cleaning solution and an air-supply pipeline serving as a flow path for the cleaning gas are provided. These pipelines are merged near the tip of the endoscope insertion part 24, and the merged pipelines are connected to the injection nozzle 54.

Note that only one pipeline denoted as a reference numeral 51 is shown in FIG. 1 as a representative of the liquid-supply pipeline and the air-supply pipeline formed in the endoscope insertion part 24.

A liquid-supply tube 32 and an air-supply tube 34 each have one end removably connected to the main body operating part 22. These tubes 32 and 34 are connected to the liquid-supply pipeline and the air-supply pipeline, respectively. The other end of each of the liquid-supply tube 32 and the air-supply tube 34 is connected to the air-supply/water-supply device 18. Note that the liquid-supply tube 32 and the air-supply tube 34 may be removably connected to the main body operating part 22 as being integrally formed as a multi-lumen tube.

The air-supply/water-supply device 18 is a device for controlling supply of the cleaning solution and the cleaning gas to be supplied to the rigid endoscope 12. The air-supply/water-supply device 18 is connected via a high-pressure gas tube 38 to a $CO_2$ gas cylinder 36. With the use of $CO_2$ gas supplied from the $CO_2$ gas cylinder 36, the cleaning solution and the cleaning gas are supplied. The cleaning solution and the cleaning gas supplied from the air-supply/water-supply device 18 are guided via the liquid-supply tube 32 and the air-supply tube 34, respectively, to the main body operating part 22, and are further guided via the liquid-supply pipeline and the air-supply pipeline, respectively, provided inside the main body operating part 22 and the endoscope insertion part 24 to the injection nozzle 54. Then, the cleaning solution and the cleaning gas are injected from the injection nozzle 54 toward the observation window 52. Note that, although details will be described further below, the air-supply/water-supply device 18 of the present embodiment controls supply of the cleaning solution and the cleaning gas according to a detection signal given from the processor device 14.

The pneumoperitoneum device 20 is a device for supplying $CO_2$ gas as a pneumoperitoneum gas to the inside of the body cavity. For this reason, to the pneumoperitoneum device 20, a $CO_2$ gas cylinder 43 is connected via a high-pressure gas tube 44. Also, a pneumoperitoneum tube 40 has one end connected to the pneumoperitoneum device 20, and the other end removably connected to an air-supply connector 49 of a trocar 26.

The air-supply connector 49 of the trocar 26 is connected to an insertion path 48 provided inside the trocar 26. This insertion path 48 is a path for letting the endoscope insertion part 24 inserted therein. The insertion path 48 has a base end side, which is an insertion side of the endoscope insertion part 24 (an upper side in FIG. 1), provided with a base end opening 56 and has a tip side opposite thereto (a lower side in FIG. 1) provided with a tip opening 57. The insertion path 48 is configured to have an inner diameter slightly larger than the outer diameter of the endoscope insertion part 24, and a space formed between the insertion path 48 and the endoscope insertion part 24 serves as a flow path for the pneumoperitoneum gas ($CO_2$ gas) supplied from the pneumoperitoneum device 20. Note that a gas path serving as a flow path for $CO_2$ gas may be provided separately from the insertion path 48.

The pressure of $CO_2$ gas supplied from the $CO_2$ gas cylinder 42 is reduced to a predetermined pressure at the pneumoperitoneum device 20, and this pressure-reduced $CO_2$ gas is guided via the pneumoperitoneum tube 40 to the air-supply connector 49 of the trocar 26. The pneumoperitoneum gas is further guided from the air-supply connector 49 to the insertion path 48 provided inside the trocar 26, and is supplied from the tip opening 57 formed at the tip of the insertion path 48 to the inside of the abdominal cavity. With this, when an examination or a treatment is performed by using the rigid endoscope 12 or a treatment instrument (not shown), the abdominal cavity can be inflated with the pneumoperitoneum gas at a predetermined pressure, thereby allowing a view of the endoscope and a treatment space to be ensured. Note that in view of protection of the patient, not air but $CO_2$ gas is preferably used as a pneumoperitoneum gas.

Figure 3:
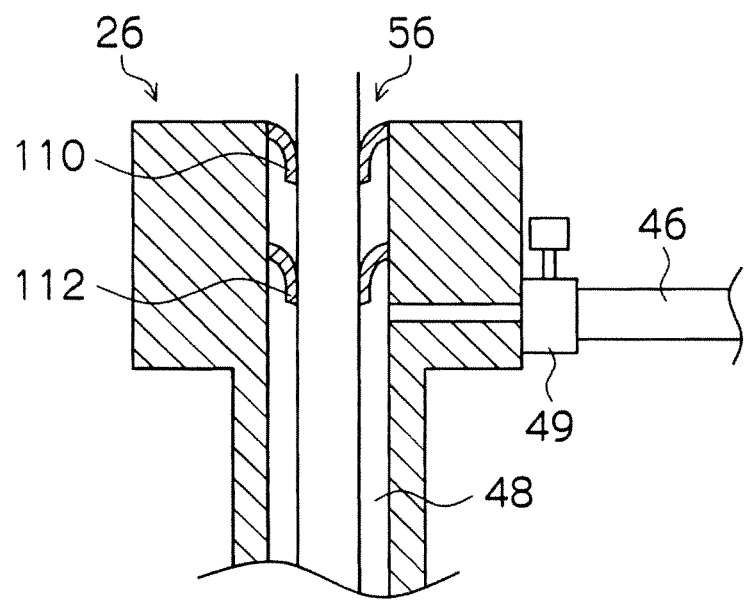
FIG. 3 is a schematic sectional view of the structure near a base end opening of a trocar.

FIG. 3 is a schematic sectional view of the structure near a base end opening of the trocar 26. As shown in FIG. 3, in the insertion path 48 of the trocar 26, first and second valve members 110 and 112 are provided near the base end opening 56. These valve members 110 and 112 are disposed as airtight means preventing the pneumoperitoneum gas guided from the air-supply connector 49 to the insertion path 48 from flowing outside from the base end opening 56. On each of the valve members 110 and 112, a slit opening is formed for allowing insertion of the endoscope insertion part 24. The shape of the slit opening is not particularly restrictive as long as it can ensure airtightness of the insertion path 48 on a tip part from the first and second valve members 110 and 112. For example, a cross-shaped slit opening as in a four-way valve may be formed, or an I-shaped slit opening may be formed. Note that while a plurality of valve members are arranged at different positions along a longitudinal direction (an axial direction) of the insertion path 48 in the present embodiment, the number of valve member is not restrictive, and one valve member may be provided, or three or more valve members may be provided. It is preferable, however, as in the present embodiment, that a plurality of valve members are arranged at different positions along the longitudinal direction of the insertion path 48, thereby allowing airtightness of the insertion path 48 to be ensured compared with the case in which one valve member is provided.

Figure 4:
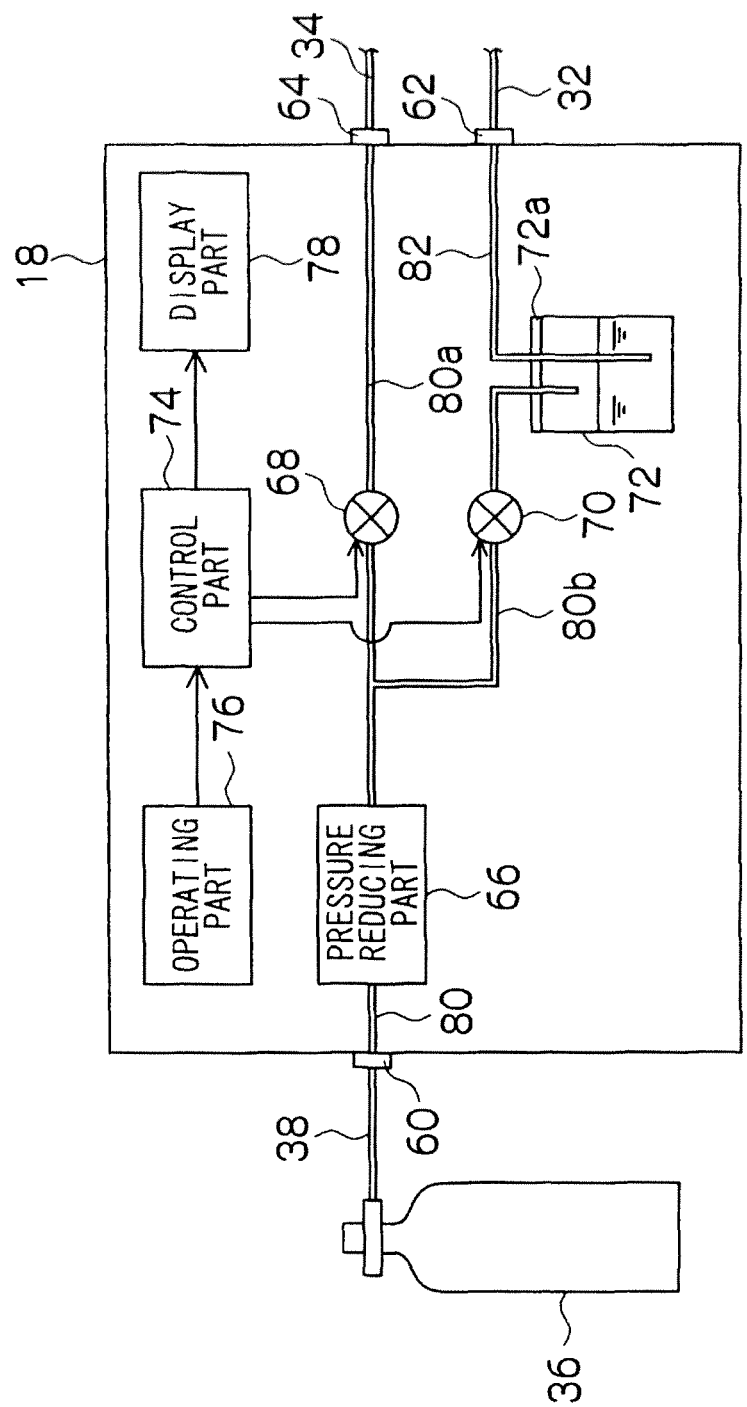
FIG. 4 is a structural diagram of an inner structure of an air-supply/water-supply device.

FIG. 4 is a structural diagram of an inner structure of the air-supply/water-supply device 18. As shown in FIG. 4, the air-supply/water-supply device 18 is provided with a plurality of connectors 60, 62, and 64 for connection with various tubes. Among these connectors 60, 62, and 64, the high-pressure connector 60 is an introduction port (an input port) for guiding $CO_2$ gas supplied from the $CO_2$ gas cylinder 36 to a gas pipeline 80 provided inside the air-supply/water-supply device 18, and has connected thereto one end of the high-pressure gas tube 38 extending from the $CO_2$ gas cylinder 36. Also, the liquid-supply connector 62 and the air-supply connector 64 are supply ports (output ports) for the cleaning solution and the cleaning gas, respectively, supplied from the air-supply/water-supply device 18, and have connected thereto one end of the liquid-supply tube 32 and the air-supply tube 34, respectively.

The air-supply/water-supply device 18 is configured to include a pressure reducing part 66, first and second solenoid valves 68 and 70, a cleaning solution tank 72, a control part 74, an operating part 76, a display part 78, and others.

The pressure reducing part 66 is provided in the midst of the gas pipeline 80 connected to the high-pressure connector 60, reducing the pressure of $CO_2$ gas supplied from the $CO_2$ gas cylinder 36 via the high-pressure connector 60 to the gas pipeline 80 to a predetermined pressure.

The gas pipeline 80 is branched on a downstream side from the pressure reducing part 66, that is, into first and second gas pipelines 80a and 80b. The first gas pipeline 80a is connected to the air-supply connector 64, in the midst of which the first solenoid valve 68 is provided. The first solenoid valve 68 is an open/close valve capable of opening and closing the first gas pipeline 80a, and opens and closes the first gas pipeline 80a according to the control signal from the control part 74, which will be described further below. With the opening/closing operation of this solenoid valve 68, the cleaning gas ($CO_2$ gas) outputted from the air-supply connector 64 is selectively supplied/stopped.

The second gas pipeline 80b is connected to the cleaning solution tank 72, in the midst of which the second solenoid valve 70 is provided. The second solenoid valve 70 is an open/close valve capable of opening and closing the second gas pipeline 80b, and opens and closes the second gas pipeline 80b according to the control signal from the control part 74, which will be described further below.

The cleaning solution tank 72 has accommodated therein the cleaning solution such as physiological saline, and is made airtight with a lid 72a. The second gas pipeline 80b has one end arranged so as to penetrate through the lid 72a to open above the liquid surface of the cleaning solution. Also, a cleaning solution supply pipeline 82 has one end arranged so as to penetrate through the lid 72a to open in the cleaning solution near the bottom of the cleaning solution tank 72. The cleaning solution supply pipeline 82 has the other end connected to the liquid-supply connector 62. With this, when $CO_2$ gas is supplied from the second gas pipeline 80b to the cleaning solution tank 72, the liquid surface of the cleaning solution accommodated in the cleaning solution tank 72 is pressurized to cause the cleaning solution to be supplied to the liquid-supply connector 62 through the cleaning solution supply pipeline 82. Therefore, with the opening/closing operation of the second solenoid valve 70, supply/stop of $CO_2$ gas from the second gas pipeline 80b to the cleaning solution tank 72 is selectively switched, thereby selectively supplying/stopping the cleaning solution outputted from the liquid-supply connector 62.

The control part 74 controls the opening/closing operation of the first and second solenoid valves 68 and 70 to control supply of the cleaning solution and the cleaning gas supplied from the air-supply/water-supply device 18. As will be described further below, the control part 74 in the present embodiment controls the opening/closing operation of the first and second solenoid valves 68 and 70 according to the detection signal given from the processor device 14.

The operating part 76 includes, for example, an operation button for manually operating supply/stop of the cleaning solution and the cleaning gas from the connectors 62 and 64, respectively, and a setting button for various settings of the air-supply/water-supply device 18. While supply of the cleaning solution and gas is automatically controlled in the present embodiment, supply of the cleaning solution and gas may be required depending on the circumstances, and therefore the cleaning solution and the cleaning gas can be supplied also with a manual operation. Therefore, by operating the operation button for manual operation, an operation signal according to the operation button is given to the control part 74, thereby controlling the opening/closing operation of the solenoid valves 68 and 70 by the control part 74.

The display part 78 displays the operation state and various setting states of the air-supply/water-supply device 18. For example, the supply state (supply/stop) of the cleaning solution and the cleaning gas supplied from the air-supply/water-supply device 18 and others are displayed.

Figure 5:
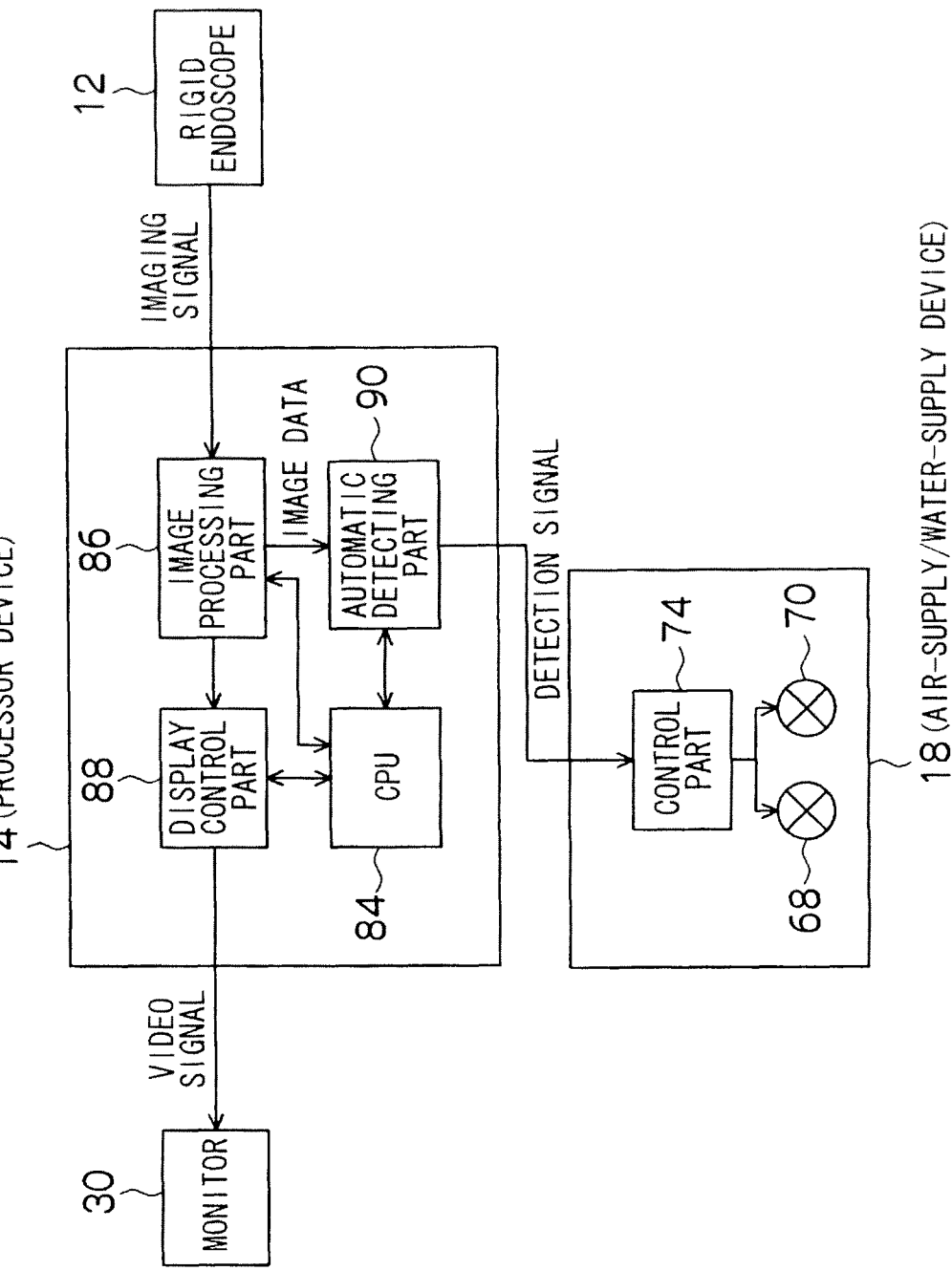
FIG. 5 is an explanatory diagram of a relation between a processor device and the air-supply/water-supply device.

Next, a relation between the processor device 14 and the air-supply/water-supply device 18 is described by using FIG. 5. As shown in FIG. 5, the processor device 14 is configured to mainly include a CPU 84, an image processing part 86, a display control part 88, and an automatic detecting part 90. Although not shown, the processor device 14 also includes a ROM having stored therein various programs and control data (such as operation data, which will be described further below) for controlling the operation of the processor device 14, a RAM having temporarily stored therein programs and data to be executed by the CPU 84, and others.

The CPU 84 is a control part that controls each part of the processor device 14 and also controls the entire endoscope system 10 in a centralized manner.

The image processing part 86 follows the control by the CPU 84 and performs color interpolation, color separation, color balance adjustment, gamma correction, image enhancing process, and other processes on an imaging signal given from the solid-state image pickup element provided at the tip of the endoscope insertion part 24 of the rigid endoscope 12 to generate image data. The image data generated at the image processing part 86 is given to the display control part 88 and the automatic detecting part 90.

The display control part 88 converts the image data given from the image processing part 86 to a video signal corresponding to a signal format supported by the monitor 30, and then outputs the video signal to the monitor 30.

The automatic detecting part 90 is a processing part that automatically detects, based on the image data given from the image processing part 86, the state in which the endoscope insertion part 24 is inserted into or removed from the insertion path 48 of the trocar 26. When determining that the tip surface 55 of the endoscope insertion part 24 is present inside the trocar 26, this automatic detecting part 90 causes a detection signal to be outputted to the control part 74 of the air-supply/water-supply device 18 to be in an ON state. On the other hand, when determining that the tip surface 55 is not present inside the trocar 26, the automatic detecting part 90 causes the detection signal to be in an OFF state. Note that various detection conditions such as a detection timing and a detection method of the automatic detecting part 90 can be changed under the control by the CPU 84.

The control part 74 of the air-supply/water-supply device 18 controls the opening/closing operation of the solenoid valves 68 and 70 according to the detection signal given from the automatic detecting part 90. Specifically, when the detection signal given from the automatic detecting part 90 is in an ON state, the control part 74 causes at least one of the first solenoid valve 68 and the second solenoid valve 70 to be in an open state. With this, the cleaning solution or the cleaning gas is supplied from the air-supply/water-supply device 18 to the rigid endoscope 12, and the cleaning solution or the cleaning gas is injected from the injection nozzle 54 of the endoscope insertion part 24, thereby cleaning the inside of the insertion path 48 of the trocar 26.

FIGS. 6A to 6D are explanatory diagrams of the state of changes of an endoscopic image when the endoscope insertion part 24 is withdrawn from the trocar 26. In each drawing, an upper portion shows a schematic sectional view when the trocar 26 and the endoscope insertion part 24 are viewed from a side surface, and a lower portion shows an endoscopic image (image data) obtained at that time.

Figure 6:
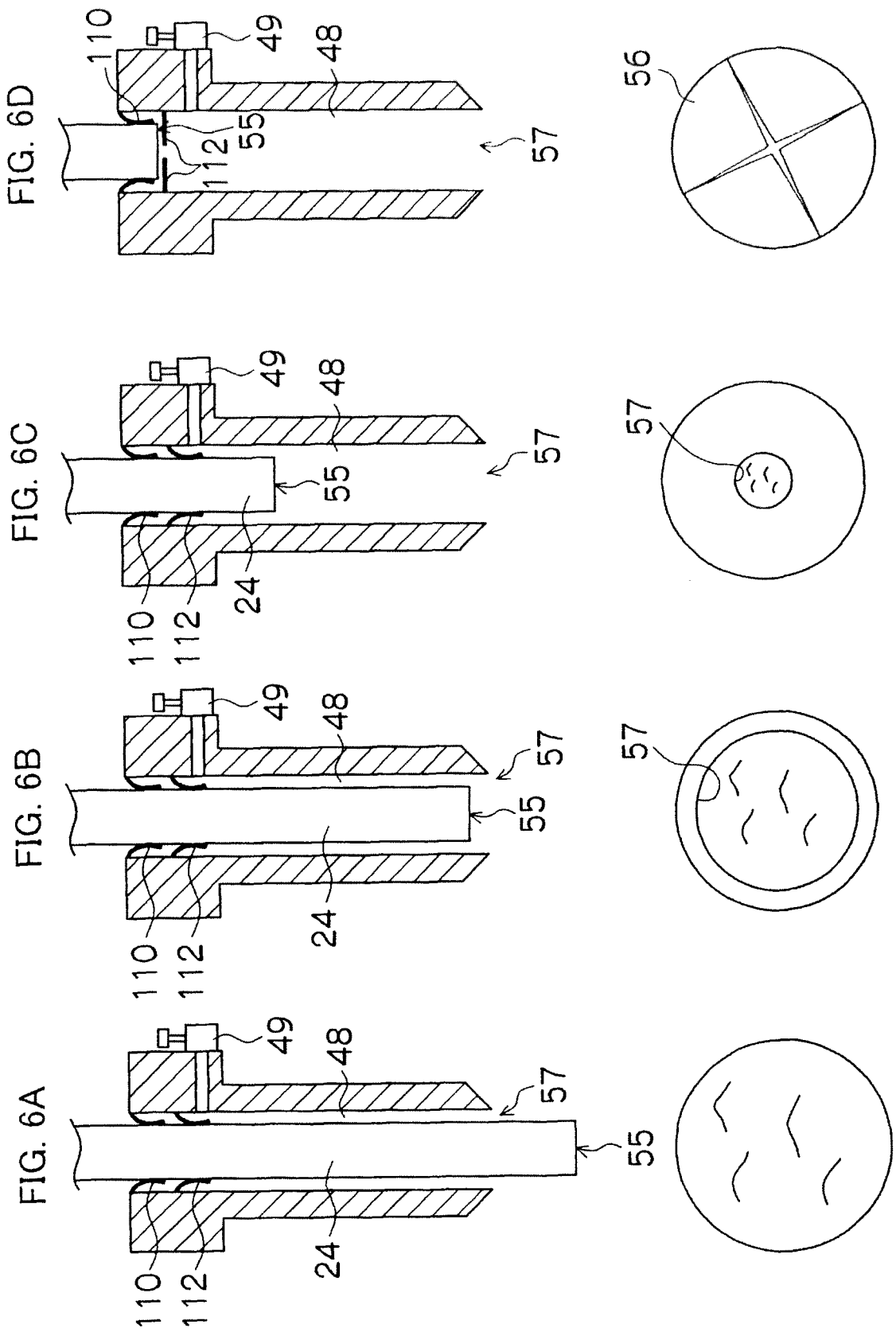
FIGS. 6A to 6D are explanatory diagrams of the state of changes of an endoscopic image when the endoscope insertion part is withdrawn from the trocar.

FIG. 6A shows the case in which the tip surface 55 of the endoscope insertion part 24 is drawn from the tip opening 57 of the trocar 26. In this case, the tip opening 57 of the trocar 26 is not included in the endoscopic image.

FIG. 6B shows the state immediately after the state in which, after the state shown in FIG. 6A, the endoscope insertion part 24 is slightly pulled up to a base end side (an upper side in FIG. 6B) and the tip surface 55 of the endoscope insertion part 24 passes through the tip opening 57 of the trocar 26. In this case, the tip opening 57 of the trocar 2 is included in the endoscopic image. Therefore, by detecting a timing when this outline shape of the tip opening 57 appears in the endoscopic image, it can be automatically detected that the tip surface 55 of the endoscope insertion part 24 has entered the inside of the trocar 26.

FIG. 6C shows the case in which, after the state shown in FIG. 6B, the endoscope insertion part 24 is further pulled up to the base end side. In this case, the opening diameter of the tip opening 57 of the trocar 26 is decreased according to the distance from the tip opening 57. Therefore, from the size of this opening diameter and its change amount, a distance from the tip opening 57 of the trocar 26 to the tip surface 55 of the endoscope insertion part 24 and an insertion/removal speed can be calculated. With this, the position of the tip surface 55 of the endoscope insertion part 24 in the trocar 26 can be easily grasped, and the process of cleaning the inside of the trocar 26 can be controlled according to that position. For example, the process of cleaning the inside of the trocar 26 may be performed during a period from the time when the tip surface 55 of the endoscope insertion part 24 passes through the tip opening 57 of the trocar 26 to the time when the endoscope insertion part 24 is pulled up through the trocar 26 a predetermined distance.

FIG. 6D shows the state in which the tip surface 55 of the endoscope insertion part 24 is positioned between the first valve member 110 and the second valve member 112. In this state, not the tip opening 57 but the second valve member 112 appears in the endoscopic image. Therefore, by detecting a timing when the second valve member 112 appears in the endoscopic image, it may be determined that the endoscope insertion part 24 has been withdrawn from the trocar 26 and the process of cleaning the inside of the trocar 26 may be stopped.

As such, from a change in the endoscopic image when the endoscope insertion part 24 is withdrawn from the trocar 26, it can be automatically detected whether the tip surface 55 of the endoscope insertion part 24 is present inside the trocar 26. Note that as for an endoscopic image when the endoscope insertion part 24 is inserted into the trocar 26, the image changes in an order in reverse to the order shown in FIGS. 6A to 6D (that is, FIG. 6D→FIG. 6C→FIG. 6B→FIG. 6A), and therefore, similarly, from a change in the endoscopic image, it can be automatically detected whether the tip surface 55 of the endoscope insertion part 24 is present inside the trocar 26.

Next, described is the process of cleaning the inside of the trocar 26 to be performed when it is detected by the detecting process described above that the tip surface 55 of the endoscope insertion part 24 is present inside the trocar 26.

Figure 7:
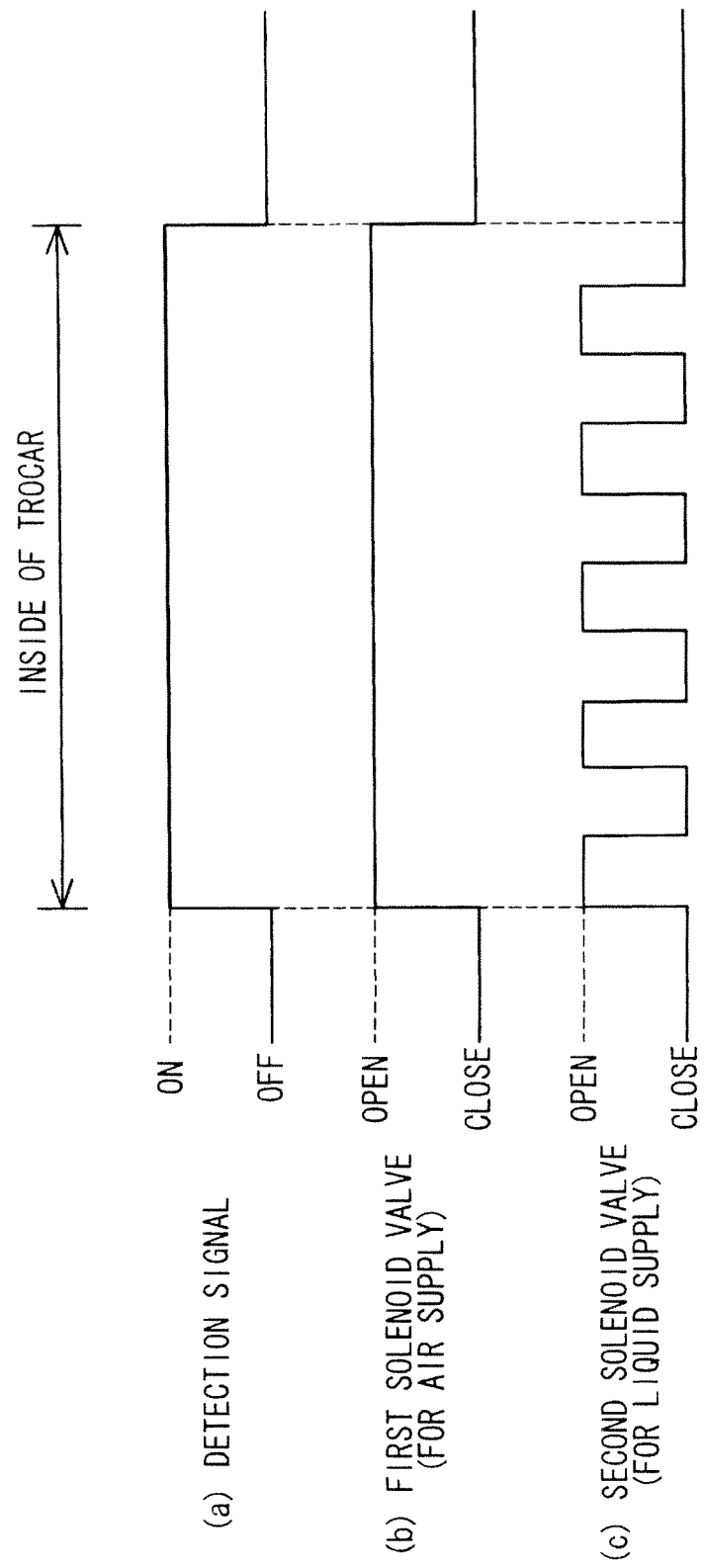
FIG. 7 is a timing chart diagram showing an example of open/close timings of solenoid valves.

FIG. 7 is a timing chart diagram showing an example of open/close timings of the solenoid valves 68 and 70. Note that opening/closing of the solenoid valves 68 and 70 shown in FIG. 7 are controlled by the control part 74 of the air-supply/water-supply device 18. In the example shown in FIG. 7, the first solenoid valve 68 is set always in an open state while the detection signal sent from the automatic detecting part 90 is being in an ON state, that is, when it is determined that the tip surface 55 of the endoscope insertion part 24 is present inside the trocar 26. On the other hand, the second solenoid valve 70 is repeatedly opened and closed at predetermined intervals. With this, a mixture fluid of the cleaning solution and the cleaning gas is injected from the injection nozzle 54 when the first and second solenoid valves 68 and 70 are open, and the cleaning gas is injected from the injection nozzle 54 when only the first solenoid valve 68 is open. Therefore, cleaning and drying the inside of the trocar 26 are alternately repeated, thereby cleaning the inside of the trocar 26.

Figure 8:
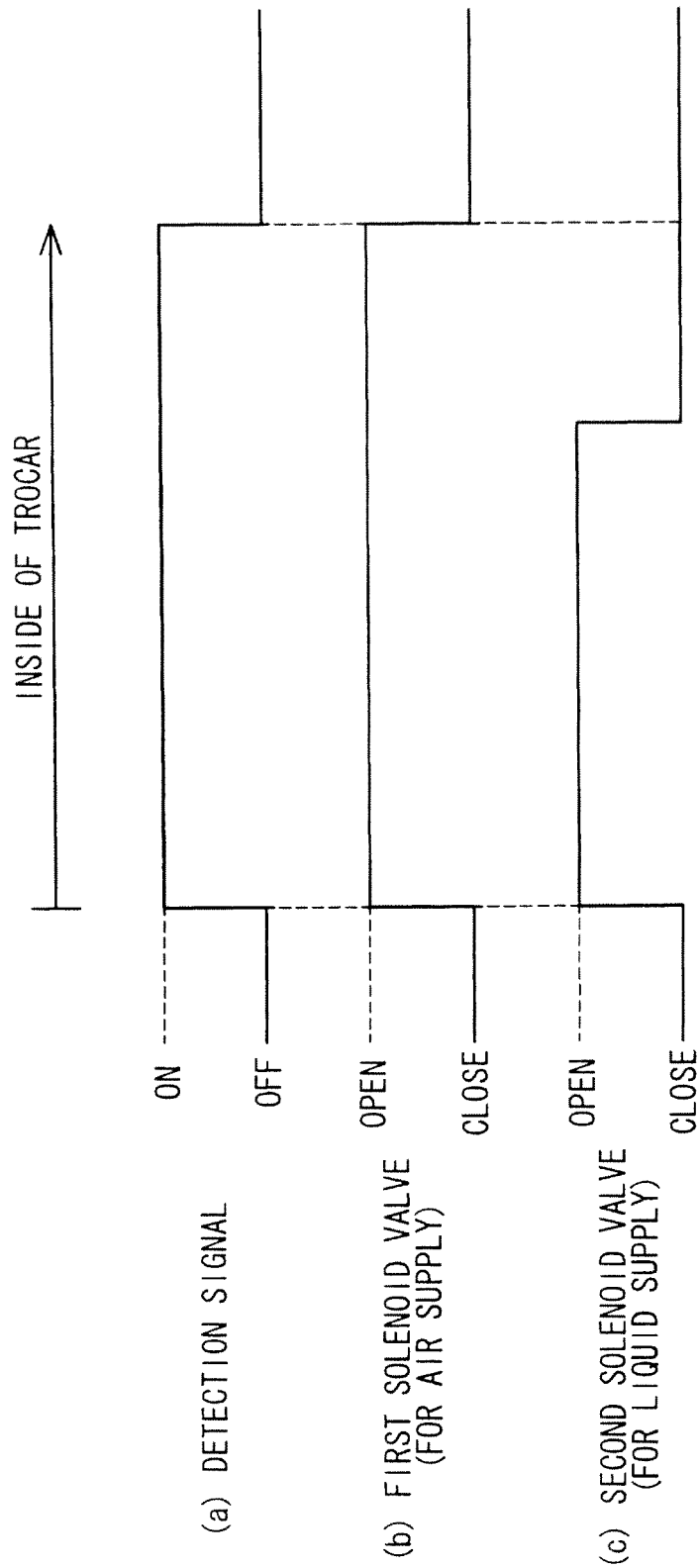
FIG. 8 is a timing chart diagram showing another example of open/close timings of the solenoid valves.

Another example of open/close timings of the solenoid valves 68 and 70 is shown in FIG. 8. In the example shown in FIG. 8, the first solenoid valve 68 is set always in an open state while the detection signal sent from the automatic detecting part 90 is being in an ON state. On the other hand, the second solenoid valve 70 is set in an open state until a predetermined time passes after the detection signal sent from the automatic detecting part 90 becomes in an ON state, but in a closed state after the lapse of the predetermined time. According to the example shown in FIG. 8, a mixture fluid of the cleaning solution and the cleaning gas is continuously injected from the injection nozzle 54 until the predetermined time passes after it is detected that the tip surface 55 of the endoscope insertion part 24 is present inside the trocar 26. Therefore, the effect of cleaning the inside of the trocar 26 is high, thereby allowing reliable prevention of transfer and retransfer of the smudges attached to the observation window 52 of the endoscope insertion part 24. Also, since only the cleaning gas is injected from the injection nozzle 54 after the predetermined time passes, drops attached inside the trocar 26 can be blown away, thereby allowing prevention of transfer of the drops from the trocar 26 to the observation window 52 of the endoscope insertion part 24.

Although not shown, while the detection signal sent from the automatic detecting part 90 is being in an ON state, only the first solenoid valve 68 may be opened to allow the cleaning gas to be always injected from the injection nozzle 54 or, conversely, only the second solenoid valve 70 may be opened to allow the cleaning solution to be always injected from the injection nozzle 54.

As such, in the endoscope system 10 of the present embodiment, it is automatically detected, based on the endoscopic image obtained via the observation window 52 of the endoscope insertion part 24, whether the tip surface 55 of the endoscope insertion part 24 is present inside (the insertion path 48 of) the trocar 26. That is, it is automatically detected whether the tip surface 55 of the endoscope insertion part 24 has been withdrawn inside the trocar 26. For this reason, no special function is required to be added to the trocar 26, and the insertion/removal operation of the endoscope insertion part into or from the trocar 26 can be easily detected. With this, it is possible to prevent an increase in size (diameter) of the trocar 26 without making the structure of the trocar 26 complex.

Also, according to the detection result described above, when the tip surface 55 of the endoscope insertion part 24 is present inside the trocar 26, the cleaning solution or the cleaning gas is automatically (forcibly) injected from the injection nozzle 54 of the endoscope insertion part 24. With this, the smudges such as blood and body fluids attached to the observation window 52 of the endoscope insertion part 24 are prevented from being transferred to the trocar 26 when the endoscope insertion part 24 is withdrawn from the trocar 26. It is also possible to prevent the smudges from being attached from the trocar 26 to the observation window 52 of the endoscope insertion part 24 when the endoscope insertion part 24 is inserted again into the trocar 26 after the smudges on the observation window 52 of the endoscope insertion part 24 withdrawn from the trocar 26 are wiped off. Therefore, without performing a special operation, the observation window 52 of the endoscope insertion part 24 inserted in the body cavity via the trocar 26 can be always kept in a good state.

Note that while a detection whether the tip surface 55 of the endoscope insertion part 24 is present inside the trocar 26 is made based on the endoscopic image obtained via the observation window 52 of the endoscope insertion part 24 in the present embodiment, this is not meant to be restrictive. Alternatively, an optical, mechanical, or magnetic detection sensor or others may be provided to the trocar 26, and a detection whether the tip surface 55 of the endoscope insertion part 24 is present inside the trocar 26 may be made according to the detection result of the detection sensor.

<Second Embodiment>

Next, a second embodiment of the present invention is described. In the following, parts common to the first embodiment are not described, and characteristic parts of the present invention are mainly described.

Figure 9:
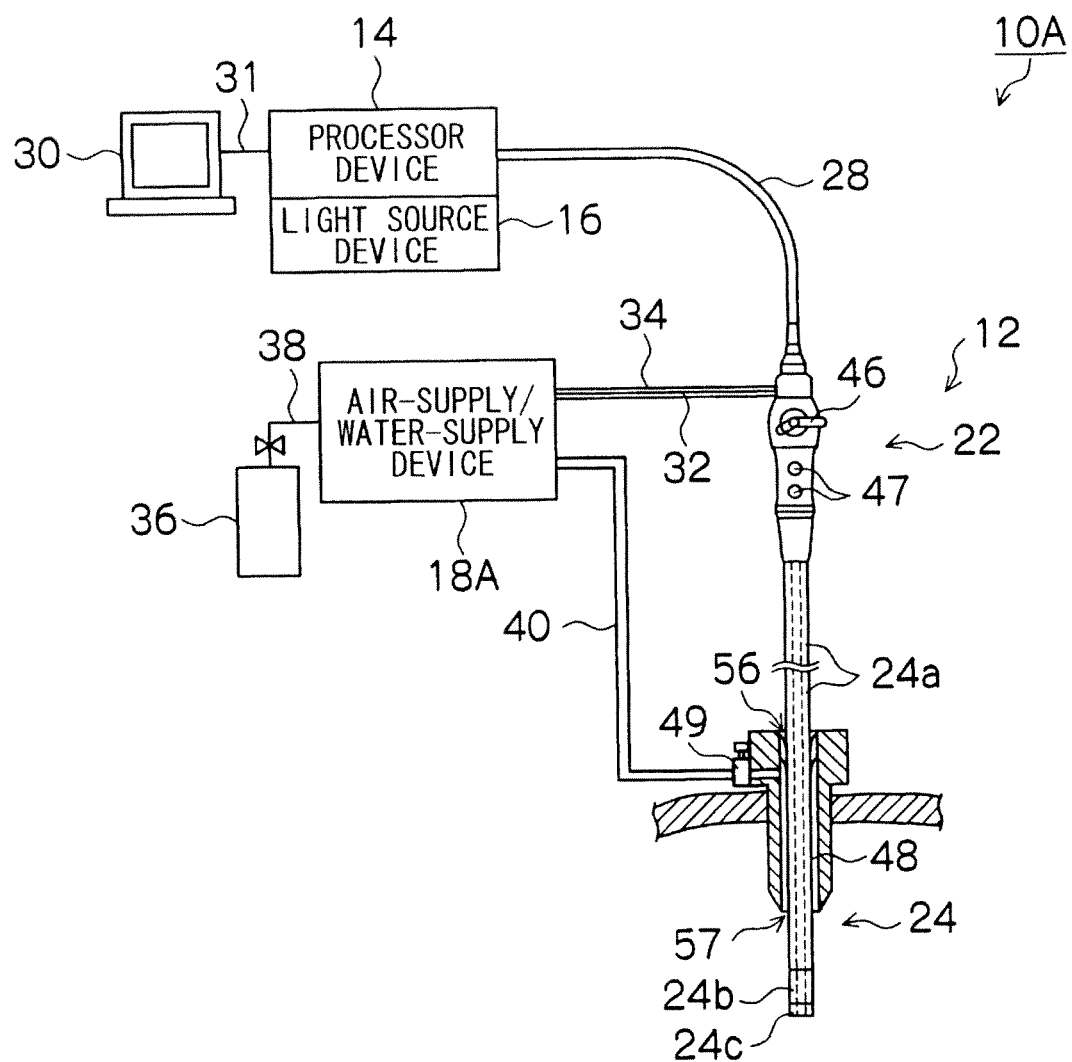
FIG. 9 is a schematic diagram of the structure of an endoscope system according to a second embodiment.

FIG. 9 is a schematic diagram of the structure of an endoscope system according to the second embodiment. In FIG. 9, components common or similar to those of FIG. 1 are provided with the same reference numeral.

As shown in FIG. 9, in an endoscope system 10A of the second embodiment, an air-supply/water-supply device 18A has not only a function of supplying the cleaning solution and the cleaning gas but also a function of supplying a pneumoperitoneum gas. By using $CO_2$ gas supplied for the $CO_2$ gas cylinder 36 as a common gas supply source, these fluids are supplied.

Figure 10:
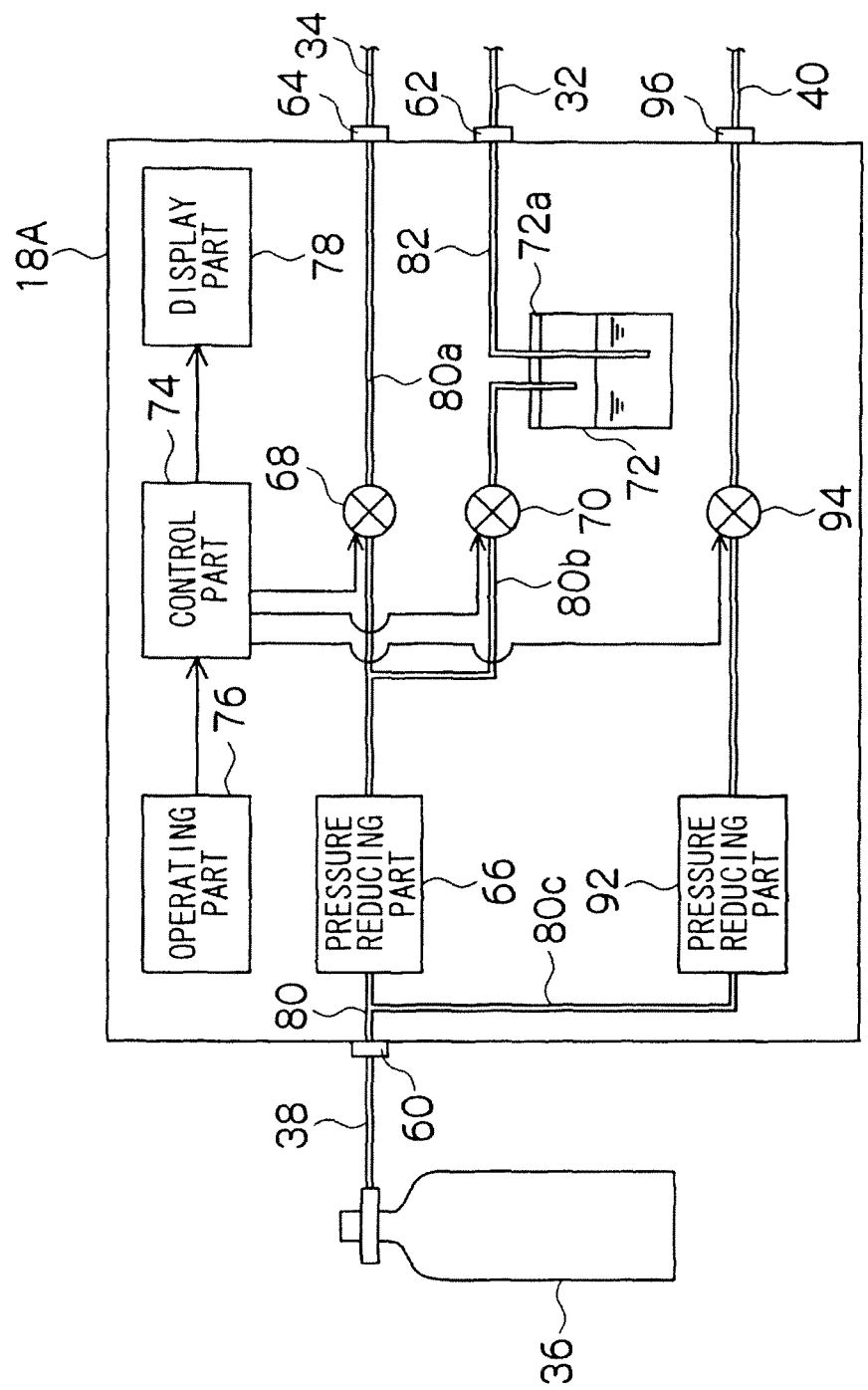
FIG. 10 is a block diagram of an inner structure of an air-supply/water-supply device in the second embodiment.

FIG. 10 is a block diagram of the inner structure of the air-supply/water-supply device 18A in the second embodiment. In the air-supply/water-supply device 18A shown in FIG. 10, in addition to the structure of the air-supply/water-supply device 18 of the first embodiment, a second pressure reducing part 92, a third solenoid valve 94, and a pneumoperitoneum gas connector 96 are further provided.

The gas pipeline 80 is branched into a third gas pipeline 80c between the high-pressure connector 60 and the pressure reducing part (a first pressure reducing part) 66, and the third gas pipeline 80c has the other end connected to the pneumoperitoneum gas connector 96. Note that one end of the pneumoperitoneum tube 40 is connected to the pneumoperitoneum gas connector 96.

The second pressure reducing part 92 and the third solenoid valve 94 are sequentially provided in the midst of third gas pipeline 80c. The second pressure reducing part 92 reduces the pressure of $CO_2$ gas flowing through the third gas pipeline 80c to a pressure suitable for a pneumoperitoneum pressure. The third solenoid valve 94 is an open/close valve capable of opening and closing the third gas pipeline 80c, and opens and closes the third gas pipeline 80c according to the control signal from the control part 74. With this opening/closing operation of this solenoid valve 94, the pneumoperitoneum gas ($CO_2$ gas) outputted from the pneumoperitoneum gas connector 96 is automatically supplied/stopped.

Figure 11:
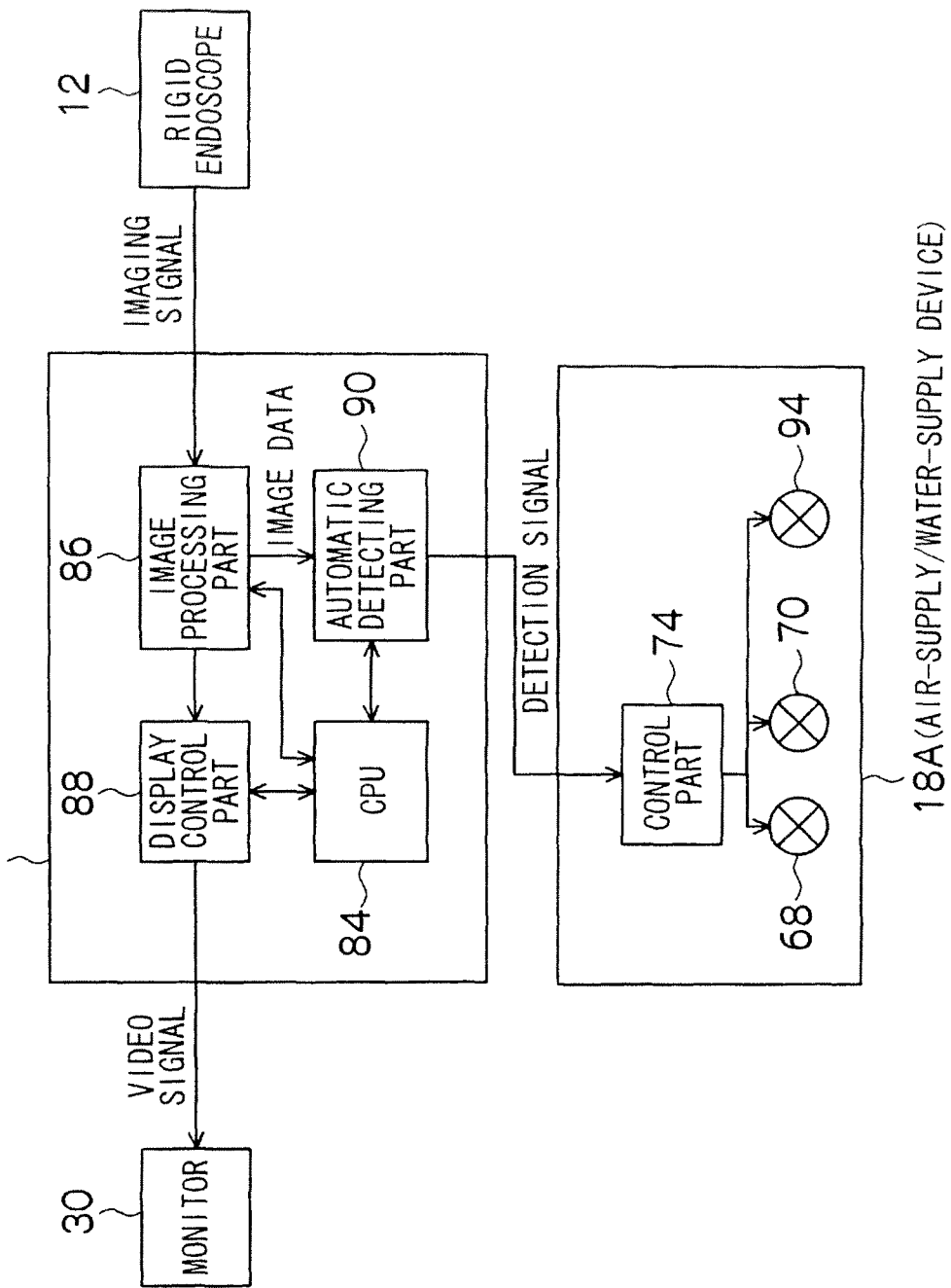
FIG. 11 is a functional block diagram of a relation between a processor device and an air-supply/water-supply device.

FIG. 11 is a functional block diagram of a relation between the processor device 14 and the air-supply/water-supply device 18A. As shown in FIG. 11, the control part 74 of the air-supply/water-supply device 18A controls opening/closing of the first to third solenoid valves 68, 70, and 94 according to the detection signal sent from the automatic detecting part 90 of the processor device 14. The detecting process to be performed at the automatic detecting part 90 of the processor device 14 is similar to that of the first embodiment.

Figure 12:
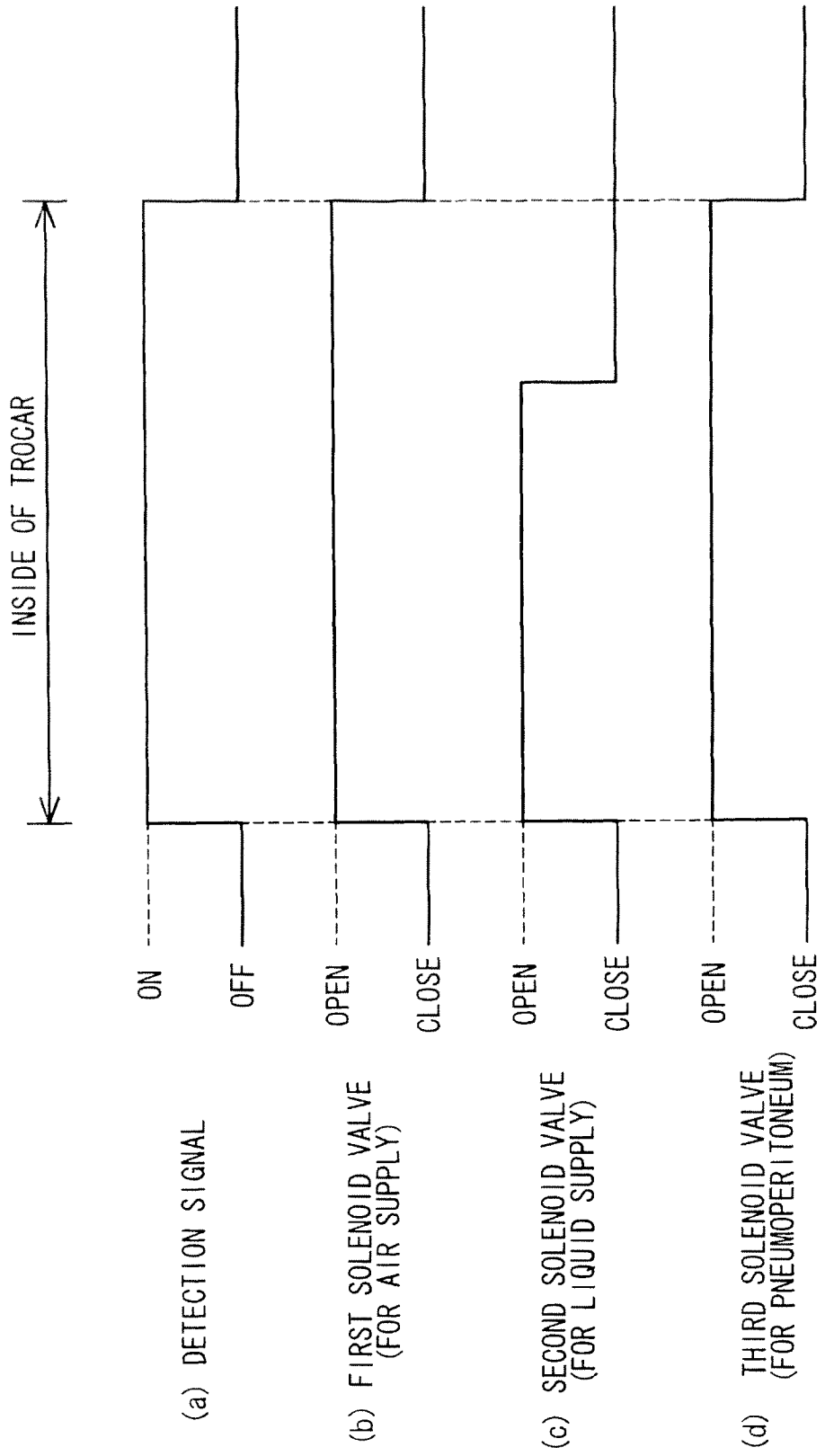
FIG. 12 is a timing chart diagram of an example of open/close timings of solenoid valves in the second embodiment.

FIG. 12 is a timing chart diagram of an example of open/close timings of the solenoid valves 68, 70, and 94 in the second embodiment. In the example shown in FIG. 12, when it is detected that the tip surface 55 of the endoscope insertion part 24 is present inside the trocar 26, that is, while the detection signal is being in an ON state, the third solenoid valve 94 is set to be always in an open state, and the pneumoperitoneum gas is always supplied from the pneumoperitoneum gas connector 96 via the pneumoperitoneum tube 40 and the air-supply connector 49 to the inside of the insertion path 48 of the trocar 26. With this, a flow of the pneumoperitoneum gas is formed on an inner wall surface of the insertion path 48 and, with a synergetic effect of injection of the cleaning solution and the cleaning gas from the injection nozzle 54 of the endoscope insertion part 24, it is possible to more reliably prevent attachment of smudges such as blood and body fluids.

Note that while the cleaning solution or the cleaning gas is injected from the injection nozzle 54 together with the pneumoperitoneum gas when it is detected that the tip surface 55 of the endoscope insertion part 24 is present inside the trocar 26 in the present embodiment, this is not meant to be restrictive, and only the penumoperitoneum gas may be forcibly supplied to the insertion path 48 in the trocar 26. Also in this case, it is possible to achieve an effect of preventing smudges from being attached in the trocar 26.

Also, in the present embodiment, since various fluids are supplied from a common gas supply source, cost can be decreased. Also, by providing commonality of the respective parts, an increase in size of the device can be prevented, and the device space can be effectively utilized.

<Third Embodiment>

Next, a third embodiment of the present invention is described. In the following, parts common to the first and second embodiments are not described and characteristic parts of the present embodiment are mainly described.

Figure 13:
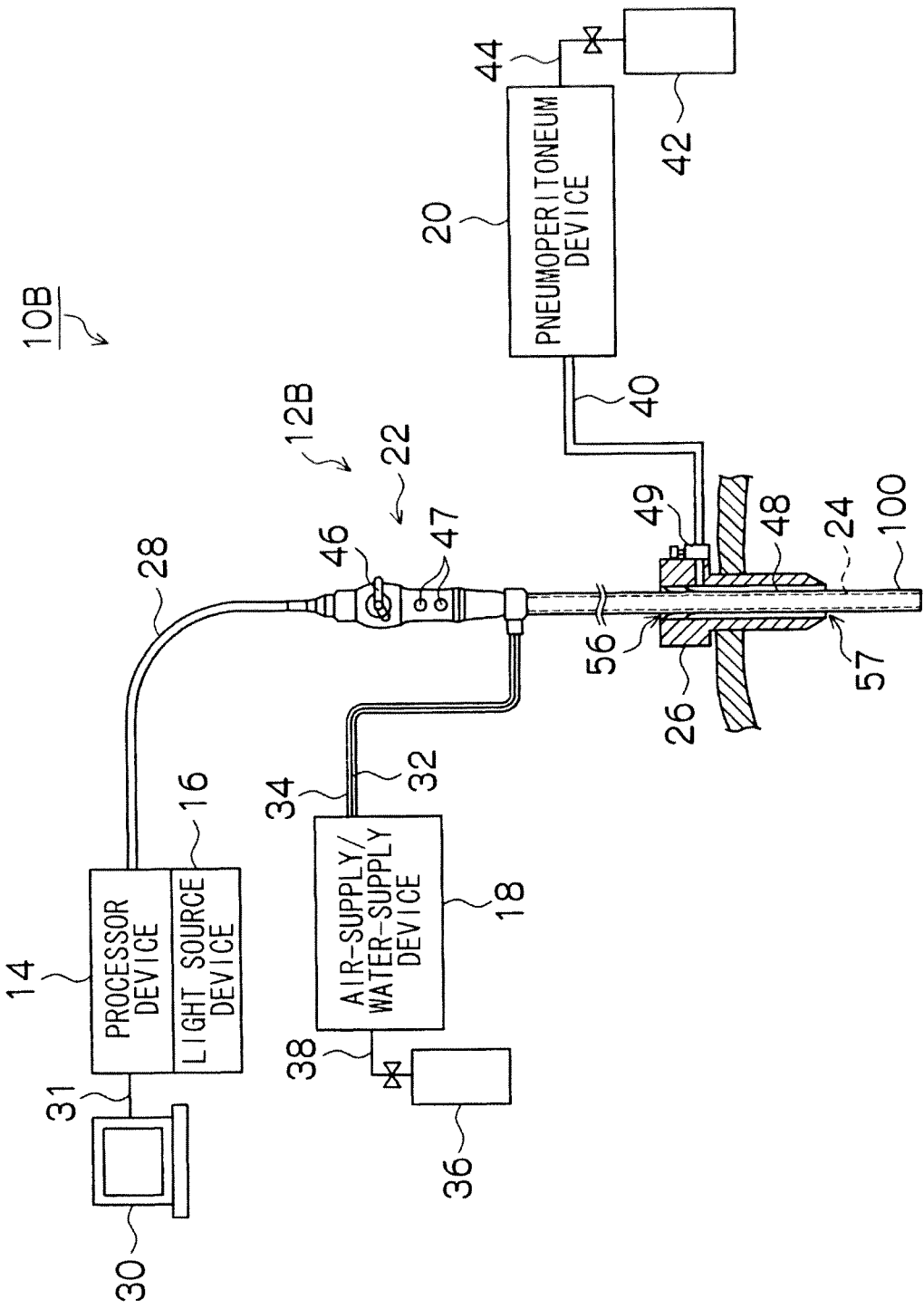
FIG. 13 is a schematic diagram of the structure of an endoscope system according to a third embodiment.
Figure 14:
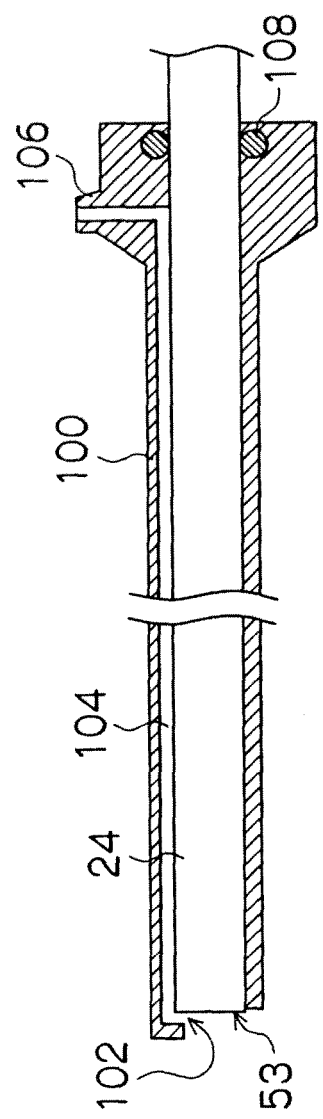
FIG. 14 is a schematic sectional view of the structure of an endoscope insertion part and a sheath covering the endoscope insertion part shown in FIG. 13.

FIG. 13 is a schematic diagram of the structure of an endoscope system 10B according to the third embodiment. FIG. 14 is a schematic sectional view of the structure of the endoscope insertion part 24 and a sheath 100 covering the endoscope insertion part 24 shown in FIG. 13.

In the third embodiment, the endoscope insertion part 24 is covered with the sheath 100. This sheath 100 has a tip provided with a nozzle 102 as means injecting a cleaning solution and a cleaning gas for removing smudges attached to the surface of the observation window 52 of the endoscope insertion part 24. This nozzle 102 is bent approximately at the right angle with respect to a sheath axial direction, and opens toward the observation window 52 of the endoscope insertion part 24 inserted in this sheath 100. This sheath 100 has a space formed therein between itself and the endoscope insertion part 24, and this space forms a fluid pipeline 104 for guiding a fluid to the nozzle 102. This fluid pipeline 104 is formed along the sheath axial direction, and is connected to the nozzle 102 provided at the tip of the sheath 100. The sheath 100 has a base end to which the liquid-supply tube 32 and the air-supply tube 34 are removably connected via a connector 106, and these tubes are connected to the fluid pipeline 104 formed inside the sheath 100. Note in FIG. 14 that a reference numeral 108 denotes an O-shaped ring, which is provided to ensure airtightness of the fluid pipeline 104. With this, the cleaning solution and the cleaning gas supplied from the air-supply/water-supply device 18 are guided to the nozzle 102 via the fluid pipeline 104 and injected from the nozzle 102.

The detecting process and the open/close control of each solenoid valve by the processor device 14 and the air-supply/water-supply device 18 are similar to those of the first embodiment.

According to the third embodiment, even if a mechanism for cleaning the observation window 52 is not provided to the rigid endoscope 12, effects similar to those of the first embodiment can be obtained with the sheath 100 having the cleaning mechanism as structured above mounted on the endoscope insertion part 24.

While the endoscope system and the method of controlling the endoscope system according to the embodiments have been described in the foregoing, the present invention is not meant to be restricted to the examples described above and, as a matter of course, can be variously improved or modified in a range not deviating from the gist of the present invention.

What is claimed is:

1. An endoscope system comprising:
an endoscope including an insertion part having an observation window at a tip;
a trocar having an insertion path for inserting the insertion part into a body cavity;
a detecting device outputting a detection signal indicating whether or not a tip part of the insertion part is present in the insertion path based on an endoscopic image obtained by the observation window;
a trocar cleaning device determining whether or not to supply a predetermined fluid from a fluid source into the insertion path for cleaning the insertion path based on the detection signal outputted from the detecting device and automatically supplying the predetermined fluid to an inside of the insertion path when it is determined from the detection signal that the tip part of the insertion part is present inside the insertion path; and
an airtight preventive member provided at a proximal end side of the insertion path for ensuring airtightness of the insertion path,
wherein the detecting device automatically detects the insertion part disposed within the insertion path when a distal opening of the tip part is present in the endoscopic image and sends the detection signal to the trocar cleaning device to supply the predetermined fluid to the inside of the insertion path, and
wherein the detecting device automatically detects the insertion part is not disposed within the insertion path when the airtight preventive member is provided in the endoscopic image and sends the detection signal to the trocar cleaning device to stop the supply of predetermined fluid to the inside of the insertion path.

2. The endoscope system according to claim 1, wherein the trocar cleaning device intermittently supplies the predetermined fluid to the inside of the insertion path when it is determined by the detection signal that the tip part of the insertion part is present inside the insertion path.

3. The endoscope system according to claim 1, wherein the trocar cleaning device supplies the predetermined fluid to the inside of the insertion path by injecting the fluid from an injection nozzle provided at the tip of the insertion part.

4. The endoscope system according to claim 1, wherein the trocar cleaning device supplies the predetermined fluid to the inside of the insertion path by injecting the fluid from an injection nozzle provided at a tip of a sheath covering the insertion part.

5. The endoscope system according to claim 1, wherein the trocar cleaning device supplies the predetermined fluid to the inside of the insertion path via a fluid introduction port provided at the trocar.

6. The endoscope system according to claim 1, wherein the trocar cleaning device cleans the inside of the insertion path by selectively supplying a cleaning solution and a gas into the insertion path.

7. An endoscope system comprising:
an endoscope including an insertion part having an observation window at a distal end;
a trocar having an insertion path for inserting the insertion part into a body cavity;
a detecting device outputting a detection signal indicating whether or not a distal end part of the insertion part is present in the insertion path based on an endoscopic image obtained by the observation window;
a trocar cleaning device determining whether or not to supply a predetermined fluid from a fluid source into the insertion path for cleaning the insertion path based on the detection signal outputted from the detecting device and automatically supplying the predetermined fluid to an inside of the insertion path when it is determined from the detection signal that the distal end part of the insertion part is present inside the insertion path; and an airtight preventive member provided at a proximal end side of the insertion path for ensuring airtightness of the insertion path, wherein the detecting device automatically detects that the insertion part disposed within the insertion path when a distal opening of the distal end part is present in the endoscopic image and sends the detection signal to the trocar cleaning device to supply the predetermined fluid to the inside of the insertion path, and wherein the detecting device automatically detects that the insertion part is not disposed within the insertion path when the airtight preventive member is provided in the endoscopic image and sends the detection signal to the trocar cleaning device to stop the supply of predetermined fluid to the inside of the insertion path.

8. The endoscope system according to claim 7, wherein the detecting device outputs the detection signal indicating that the distal end part of the insertion part is present inside the insertion path when a tip opening of the trocar is included in the endoscopic image.

\* \* \* \* \*